US011437011B2

(12) United States Patent
Stalter et al.

(10) Patent No.: US 11,437,011 B2
(45) Date of Patent: Sep. 6, 2022

(54) APPARATUS AND METHOD FOR ACTIVE NOISE SUPPRESSION IN A VEHICLE

(71) Applicant: Dr. Ing. h.c. F. Porsche Aktiengesellschaft, Stuttgart (DE)

(72) Inventors: Frank Stalter, Renningen (DE); Luken Hemmes, Vaihingen an der Enz (DE)

(73) Assignee: Dr. Ing. h.c. F. Porsche Aktiengesellschaft

( * ) Notice: Subject to any disclaimer, the term of this patent is extended or adjusted under 35 U.S.C. 154(b) by 0 days.

(21) Appl. No.: 17/215,123

(22) Filed: Mar. 29, 2021

(65) Prior Publication Data

US 2021/0398514 A1 Dec. 23, 2021

(30) Foreign Application Priority Data

Jun. 23, 2020 (DE) ..................... 10 2020 116 451.3

(51) Int. Cl.
*G10K 11/16* (2006.01)
*G10K 11/178* (2006.01)
*A61F 11/06* (2006.01)

(52) U.S. Cl.
CPC .. *G10K 11/1785* (2018.01); *G10K 2210/1282* (2013.01)

(58) Field of Classification Search
CPC ................... G10K 11/1785; G10K 2210/1282
USPC ................................................ 381/71.1, 71.4
See application file for complete search history.

(56) References Cited

U.S. PATENT DOCUMENTS

| | | | | |
|---|---|---|---|---|
| 9,633,644 | B2 | 4/2017 | Inoue | |
| 2007/0265736 | A1 | 11/2007 | Mensler et al. | |
| 2013/0311040 | A1 | 11/2013 | Hasegawa et al. | |
| 2015/0228267 | A1 * | 8/2015 | Inoue | G10K 11/17883 381/71.4 |
| 2016/0071508 | A1 | 3/2016 | Wurm et al. | |

FOREIGN PATENT DOCUMENTS

| | | | | |
|---|---|---|---|---|
| DE | 102015202560 | A1 | 8/2015 | |
| DE | 102015016013 | A1 | 8/2016 | |
| DE | 102016208023 | A1 | 11/2017 | |
| DE | 102017207756 | A1 | 11/2018 | |
| WO | 9208223 | A1 | 5/1992 | |
| WO | WO-9208223 | A1 * | 5/1992 | G10K 11/178 |

* cited by examiner

*Primary Examiner* — Ammar T Hamid
(74) *Attorney, Agent, or Firm* — RatnerPrestia

(57) ABSTRACT

A method and an apparatus for active noise suppression in a vehicle. The apparatus includes an actuator in the vehicle and a part of the vehicle. The part of the vehicle is designed according to a first transfer function, which characterizes a transmission behavior of the part of the vehicle for sound. At least a part of the actuator is configured according to a second transfer function, which characterizes a transmission behavior of the at least one part for sound. The actuator is controllable in dependence on a control variable for active noise suppression.

14 Claims, 3 Drawing Sheets

APPARATUS AND METHOD FOR ACTIVE NOISE SUPPRESSION IN A VEHICLE

CROSS-REFERENCE TO RELATED APPLICATION

This application claims priority to German Patent Application No. 10 2020 116 451.3, filed Jun. 23, 2020, which is incorporated by reference herein in its entirety.

FIELD OF THE INVENTION

The invention relates to an apparatus and a method for active noise suppression in a vehicle.

BACKGROUND OF THE INVENTION

DE 10 2015 016 013, DE 10 2016 208 023, WO 92/08223, US 2013/311040 and DE 10 2015 202 560 disclose possibilities for noise suppression in a vehicle. Each of these references is incorporated by reference in its entirety.

SUMMARY OF THE INVENTION

A method for active noise suppression in a vehicle envisages that a control variable for an actuator of the vehicle is determined, wherein the actuator is controlled in dependence on the control variable, wherein the control variable is determined in dependence on a first transfer function, which characterizes a transmission behavior of a part of the vehicle for sound, and in dependence on a second transfer function, which characterizes a transmission behavior of at least a part of the actuator for sound, wherein, in dependence on a phase, a frequency and/or an amplitude of a sound at the vehicle, a phase, a frequency and/or an amplitude of the control variable is determined in dependence on a function having at least one parameter defined by a characteristic of the first transfer function and/or the second transfer function. Thus, in an active system, the actuator is used as an acoustic sound source to actively cancel a specific frequency, i.e. for active noise canceling. Here, the frequency and amplitude of the sound source represent the negatives of the sound to be canceled. Two parts are taken into account by the first transfer function and the second transfer function. One possibility that may be envisaged is to use a plurality of transfer functions to account for the entire assembly of the axle of the vehicle. Parts of the vehicle can thus be designed in such a way that their transfer function makes a positive contribution to reducing sound, for example by using materials in the transmission path of the sound generated by the sound source which help to produce the required amplitude and frequency. In the example, the actuator represents a primary sound source that, with an amplitude X, produces a certain acoustic intensity and, with a frequency Y, produces a certain tone. The respective part forms a body with a transmission behavior Z. The body represents a final sound source, by which sound with a new acoustic intensity Xneu and a new frequency Yneu is generated in the air surrounding the vehicle. By superposing the sound emitted by the bodies of the respective parts with the sound to be canceled, a noise modification is produced for the interior and exterior sound.

The part of the vehicle may comprise one axle component or a plurality of axle components.

The motor actuator preferably defines a first sound source, wherein at least one second sound source is arranged on the vehicle and the phase, the frequency and/or the amplitude of the control variable is determined in dependence on a phase, a frequency and/or an amplitude of a sound generated or to be generated by the at least one second sound source. A plurality of actuators can also be provided for specific partial sound sources in the overall vehicle, e.g. front axle steering for rolling noise at the front wheels or rear axle steering for rolling noise at the rear wheels+exhaust system.

The sound is preferably detected at the vehicle or modeled in dependence on a transfer function for a part of the vehicle and/or at least one operating parameter of the vehicle.

An apparatus for active noise suppression in a vehicle provides that the apparatus comprises an actuator in the vehicle and a part of the vehicle, wherein the part of the vehicle is designed according to a first transfer function, which characterizes a transmission behavior of the part of the vehicle for sound, and wherein at least a part of the actuator is configured according to a second transfer function, which characterizes a transmission behavior of the at least one part for sound, wherein the actuator is controllable in dependence on the control variable for active noise suppression.

The apparatus can comprise a sensor which is designed to detect the sound at the vehicle.

The apparatus can comprise a controller, wherein the controller is designed to determine the control variable.

BRIEF DESCRIPTION OF THE DRAWINGS

Further advantageous embodiments will become apparent from the following description and the drawing. In the drawing.

DETAILED DESCRIPTION OF THE INVENTION

Figure 1:
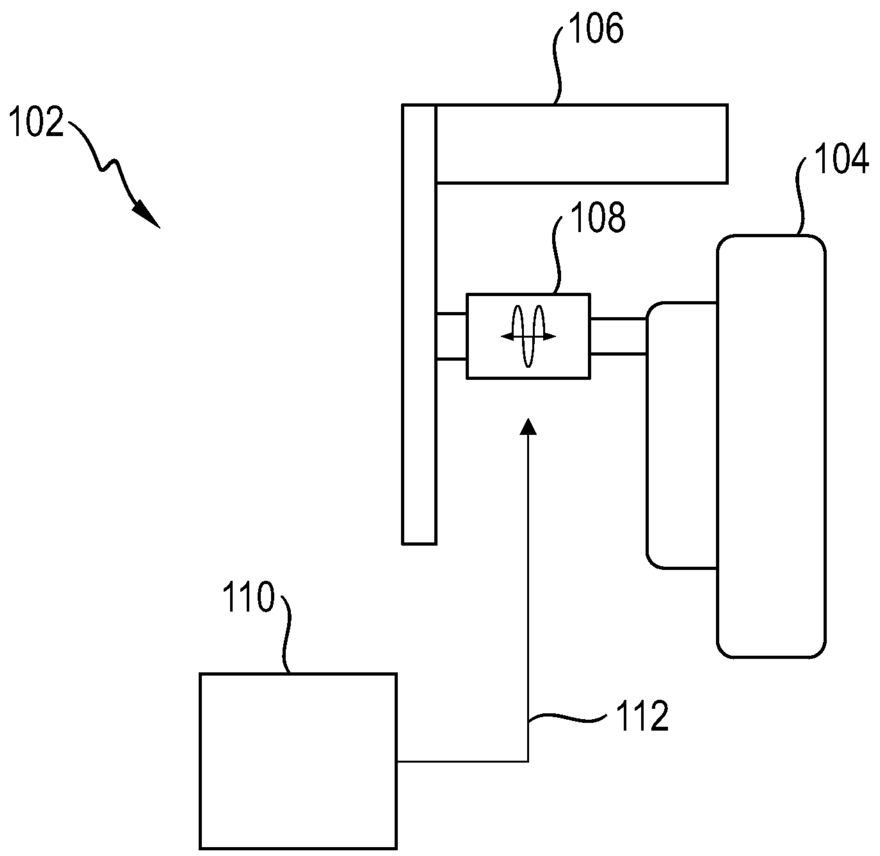
FIG. 1 shows a schematic illustration of parts of a device for noise suppression.

FIG. 1 schematically illustrates parts of an apparatus 102 for active noise suppression in a vehicle. The vehicle can include the apparatus 102. One apparatus 102 can be arranged at each wheel of the vehicle.

The apparatus 102 comprises at least one part of a chassis 104, a part of the vehicle 106, such as a part of a body, and an actuator 108.

The part of the vehicle 106 is designed according to a first transfer function, which characterizes a transmission behavior of the part of the vehicle 106 for sound.

The at least one part of the chassis 104 is designed according to a second transfer function, which characterizes a transmission behavior of the at least one part of the chassis 104 for sound.

The apparatus 102 can comprise a controller 110 or can be controllable by said controller by means of a control variable 112.

The actuator 108 is controllable in dependence on the control variable 112 for active noise modification in accordance with the following method. The control unit 110 is designed to determine the control variable 112 in accordance with the method.

Figure 2:
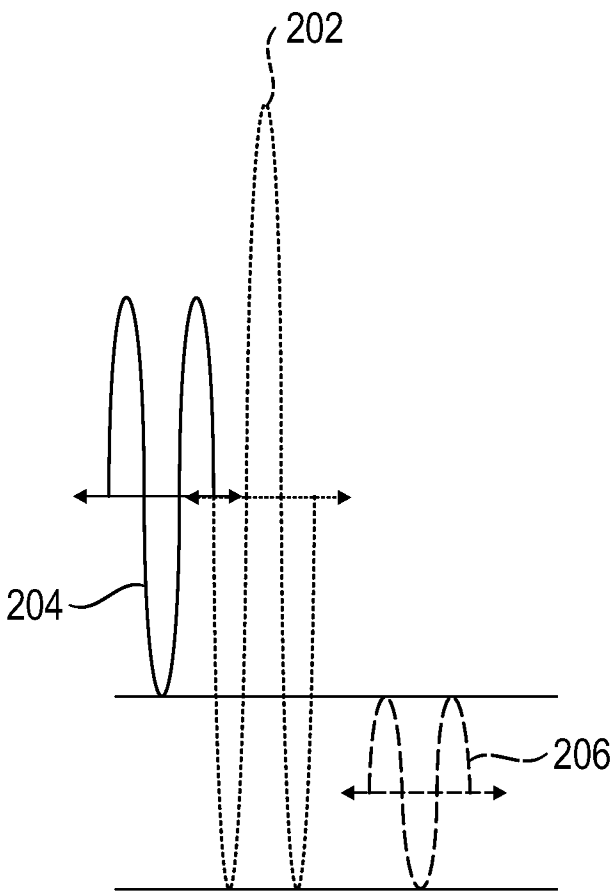
FIG. 2 shows a schematic illustration of sound signals.

It is possible to provide a sensor designed to detect a sound at the vehicle 202. The sound at the vehicle 202 is illustrated by way of example in FIG. 2. This sound to be modified at the vehicle 202 may be generated by a part of the vehicle when the vehicle is moving.

By means of the control variable 112 and its variation of this sound using the first transfer function and the second transfer function, this method generates a sound at the vehicle that cancels a sound wave at the vehicle 202 at least partially by superposition. The resulting noise 206 is likewise illustrated in FIG. 2. In the example, the sound at the vehicle 202 has a frequency Y and an amplitude X. The sound 204 generated by the control variable 112 and by the modification using the first and/or the second transfer function has, in the example, the same frequency Y and an amplitude ⅔ X. The sound 204 generated by the control variable 112 and by the modification using the first transfer function and/or the second transfer function has a phase that is 180° shifted relative to a phase of the sound at the vehicle 202. As a result, the amplitude of the resulting noise 206 is reduced to ⅓ X.

Other frequencies, amplitudes and phases can be employed to selectively influence the tone and acoustic intensity.

Figure 3:
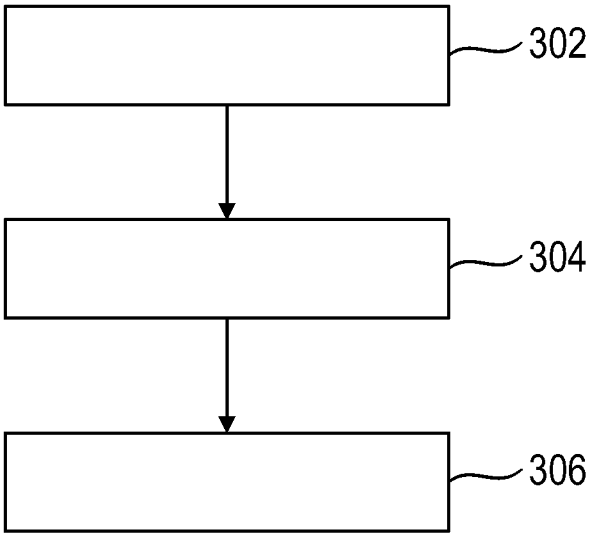
FIG. 3 shows steps in a method for noise suppression.

The method is described with reference to FIG. 3.

The method envisages that the sound is detected at the vehicle 302 or modeled in dependence on at least one operating parameter of the vehicle. The part of the vehicle 106 may comprise an axle component, an axle side member, a wheel housing, or a wheel housing shell. Their sound transmission behavior can be known for the vehicle type and therefore modeled with the second transfer function. The part of the chassis 104 may comprise a wheel carrier, a transverse link, a wheel, or a tire, the sound transmission behavior of which is likewise known and can therefore be modeled using the first transfer function.

In a step 304, the control variable 112 for the actuator 108 of the vehicle is determined.

The control variable 112 is determined in dependence on the first transfer function, which characterizes a behavior of a part of the vehicle 106, and in dependence on the second transfer function, which characterizes a behavior of the part of the chassis 104 which is mounted so as to be rotatable relative thereto. If the sound is detectable by a sensor, a determination of the control variable 112 may be made in dependence on said sound.

In dependence on a phase, a frequency, and/or an amplitude of the sound at the vehicle 202, a phase, a frequency, and/or an amplitude of the control variable 112 is determined in dependence on a function which has at least one parameter defined by a characteristic of the first transfer function and/or the second transfer function.

In a step 306, the actuator 108 is controlled in dependence on the control variable 112.

The resulting noise 206 is thereby generated.

The actuator 108 can define a first sound source, wherein at least one second sound source is arranged on the vehicle. In this case, the phase, the frequency and/or the amplitude of the control variable 112 can be determined in dependence on a phase, a frequency and/or an amplitude of a sound generated or to be generated by the at least one second sound source. An existing system can thereby be upgraded for active noise cancellation.

Provision may be made to develop parts of the vehicle according to transfer functions that meet a predetermined criterion for the resultant noise 206 for a particular type of vehicle. For example, the materials or arrangement of the parts may be selected in such a way that their transfer function, i.e., their ability to transmit sound generated by the actuator 108, compensates for noise generated by other parts of the vehicle while driving.

For example, a bearing in the transverse link may be replaced with some other bearing. As a result, the actuator 108 can be used to generate a resonance at, for example, 410 Hz, which it was not previously possible to generate. It is equally possible for the control signal 112 to be generated in such a way that, with the resonance, a reduction in the acoustic intensity of the resulting noise is achievable by virtue of the phase shift without replacing the bearing, a reduction which is advantageous for compliance with limits.

What is claimed is:

1. A method for active noise suppression in a vehicle, said method comprising the steps of:

determining a control variable for an actuator of the vehicle in dependence on a first transfer function, which characterizes a sound transmission behavior of a moving part of the vehicle, and in dependence on a second transfer function, which characterizes a sound transmission behavior of a different part of the vehicle, determining a phase, a frequency and/or an amplitude of the control variable in dependence on a function having at least one parameter defined by a characteristic of the first transfer function and the second transfer function; and controlling the actuator in dependence on the control variable.

2. The method as claimed in claim 1, wherein the different part of the vehicle comprises one axle component or a plurality of axle components.

3. The method as claimed in claim 1, wherein the actuator defines a first sound source, wherein at least one second sound source is arranged on the vehicle and the phase, the frequency and/or the amplitude of the control variable is determined in dependence on a phase, a frequency and/or an amplitude of a sound generated or to be generated by the at least one second sound source.

4. The method as claimed in claim 1, wherein the sound is detected at the vehicle or modeled in dependence on a transfer function for a part of the vehicle and/or at least one operating parameter of the vehicle.

5. An apparatus for active noise suppression in a vehicle, wherein the apparatus comprises an actuator of the vehicle, wherein a moving part of the vehicle is configured according to a first transfer function, which characterizes a sound transmission behavior of the moving part of the vehicle, and wherein a different part of the vehicle is configured according to a second transfer function, which characterizes a sound transmission behavior of the different part, wherein the actuator is controllable in dependence on a control variable for active noise suppression, wherein the control variable is determined in dependence on the first and second transfer functions.

6. The apparatus as claimed in claim 5, wherein the apparatus comprises a sensor which is configured to detect a sound at the vehicle.

7. The apparatus as claimed in claim 5, wherein the apparatus comprises a controller configured to determine the control variable.

8. A vehicle comprising the apparatus as claimed in claim 5.

9. The method as claimed in claim 1, wherein the actuator is a steering actuator.

10. The method as claimed in claim 1, wherein the moving part is a wheel carrier, a wheel, or a tire.

11. The method as claimed in claim 1, wherein the different part is an axle component, an axle side member, a wheel housing, or a wheel housing shell.

12. The apparatus as claimed in claim 5, wherein the actuator is a steering actuator.

13. The apparatus as claimed in claim 5, wherein the moving part is a wheel carrier, a wheel, or a tire.

14. The apparatus as claimed in claim 5, wherein the different part is an axle component, an axle side member, a wheel housing, or a wheel housing shell.

* * * * *